United States Patent [19]

Anderson

[11] 4,407,296

[45] Oct. 4, 1983

[54] INTEGRAL HERMETIC IMPANTABLE PRESSURE TRANSDUCER

[75] Inventor: Kenneth M. Anderson, Bloomington, Minn.

[73] Assignee: Medtronic, Inc., Minneapolis, Minn.

[21] Appl. No.: 186,373

[22] Filed: Sep. 12, 1980

[51] Int. Cl.³ .............................................. A61B 5/02
[52] U.S. Cl. .................................. 128/675; 128/748; 73/706; 73/726
[58] Field of Search ...................... 128/673, 675, 740; 73/706, 720, 721, 726, 727

[56] References Cited

U.S. PATENT DOCUMENTS

| | | | |
|---|---|---|---|
| 2,796,863 | 6/1957 | Wittern | 128/675 |
| 3,038,465 | 6/1962 | Allard et al. | 128/675 |
| 3,051,896 | 8/1962 | Bieganski | 128/748 X |
| 3,240,207 | 3/1966 | Barker et al. | 128/675 |
| 3,242,449 | 3/1966 | Stedman | 128/675 |
| 3,349,623 | 10/1967 | Pastan | 128/675 X |
| 3,614,954 | 10/1971 | Mirowski et al. | 128/419 |
| 3,811,427 | 5/1974 | Kresse | 73/720 X |
| 3,811,429 | 5/1974 | Fletcher | 73/720 X |
| 3,939,823 | 2/1976 | Kaye et al. | 73/726 X |
| 3,946,724 | 3/1976 | Le Balme | 128/675 |
| 4,006,735 | 2/1977 | Hittman et al. | 128/748 |
| 4,023,562 | 5/1977 | Hynecek et al. | 73/727 X |
| 4,263,252 | 5/1981 | Chubbuek et al. | 128/748 |

Primary Examiner—Lee S. Cohen
Attorney, Agent, or Firm—Reed A. Duthler; John L. Rooney; Joseph F. Breimayer

[57] ABSTRACT

A hermetically sealed pressure transducer suitable for implantation in a human body. A pressure sensitive circuit is fabricated using contemporary silicon technology. The pressure sensitive circuit is sealed in an oil-filled chamber formed within a titanium cylinder having a glass substrate bottom and a thin titanium top. According to one embodiment, the pressure sensitive circuit contains a sealed inner chamber at a known pressure, thereby measuring pressure relative to a known value. A second embodiment vents the pressure sensitive circuit to produce a relative pressure measurement. A grill protects the assembly and aids insertion into the desired area. A lead connects the transducer to an implantable sensing circuit.

7 Claims, 12 Drawing Figures

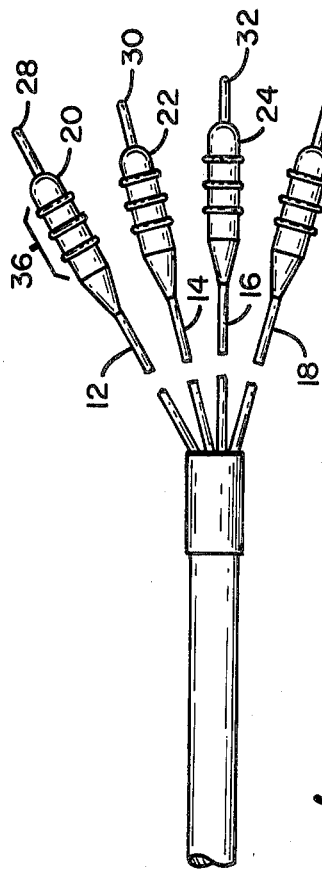
Fig. 1
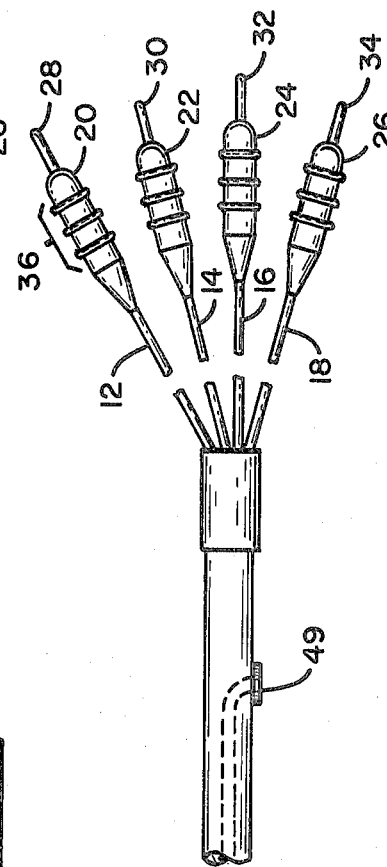
Fig. 11
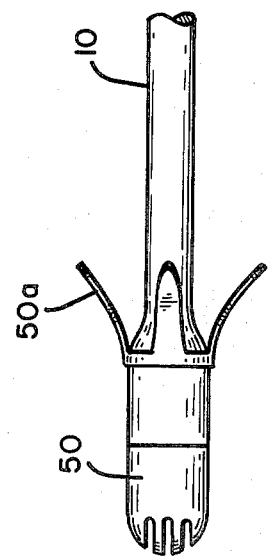
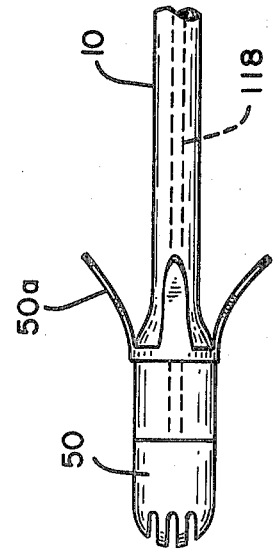

INTEGRAL HERMETIC IMPANTABLE PRESSURE TRANSDUCER

BACKGROUND OF THE INVENTION

1. Field of the Invention—The present invention relates generally to devices for measurement of fluid pressures internal to the body and more specifically relates to a miniature pressure sensor which is hermetically sealed for chronic implantation.

2. Description of the Prior Art—The need for measuring the pressure of fluids internal to the human body has long existed. The earliest successful method, and indeed still most prevalent, is through the use of a catheter. U.S. Pat. No. 3,473,386 issued to H. A. Neilsen, et al, describes apparatus for measuring through a catheter. A major disadvantage of the catheter is the lack of accuracy.

Implantable pressure transducers are now commercially available. U.S. Pat. No. 4,023,562 issued to Hynecek, et al, describes such an implantable pressure transducer. Unfortunately, the device disclosed by Hynecek, et al is not suitable for chronic implantation as body fluids destroy the pressure transducer over time.

The problem to be thus solved is the packaging of a pressure transducer similar to that disclosed by Hynecek, et al, in a form suitable for chronic implantation.

SUMMARY OF THE INVENTION

A monolithic, silicon-based, piezoresistive semiconductor element is shown as the basic pressure transducer although a piezocapactive element could also be used. The basic pressure transducer is attached to a glass substrate via adhesive. Electrical conductors which pass through the glass substrate are wire bonded to the basic pressure transducer. The glass substrate is welded to seal one end of a titanium cylinder. Although other metals such as stainless steel could be used, titanium is specified because it does not corrode in the body. A very thin diaphragm of titanium is welded to the titanium cylinder to seal the other end. The chamber thus created, which contains the basic pressure transducer, is vacuum filled with oil. Pressure of a fluid impinging upon the titanium diaphragm is transmitted to the basic pressure transducer via the oil.

The titanium diaphragm is protected from damage by a titanium grill, which also assists in insertion for transvenous application. Since is does not act as a hermetic seal, the grill could also be a polymer like urethane. Tines, loops, or other additions may be made to aid in anchoring the assembly in the desired position.

The sealed pressure transducer assembly is attached to leads which electrically couple the basic pressure transducer to implantable electrode circuitry. A first embodiment seals an inner chamber within the basic pressure transducer with the result that pressure measurements are made relative to the sealed pressure. Calibration of the inner chamber pressure is accomplished at the time of manufacture. A second embodiment vents the inner chamber of the basic pressure transducer to an area, such as the abdominal cavity, providing differential pressure measurement. The pressure vent is also oil-filled with the oil coupling the inner chamber of the basic pressure transducer to the area of differential pressure via an oil-filled tube in the lead and a silastic membrane.

BRIEF DESCRIPTION OF THE DRAWINGS

FIG. 1 is a schematic view of the preferred embodiment of the entire pressure sensing lead.

FIG. 11 is a schematic view of the alternative embodiment of the entire pressure sensing lead.

DESCRIPTION OF THE PREFERRED EMBODIMENTS

Figure 2:
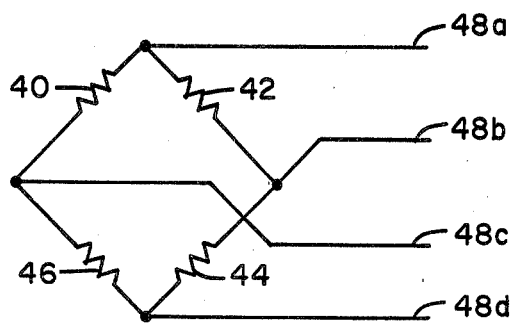
FIG. 2 is an electrical equivalency diagram of the pressure transducer.

The present invention is described as embodied in two implantable pressure transducer leads. The first contains a sealed inner chamber having a calibrated pressure. The second is vented via the lead to permit measurement of the differential pressures. Those skilled in the art will be able to adapt the present invention for their specific applications based upon the following detailed description.

FIG. 1 shows the lead having the sealed inner chamber. The pressure transducer head 50 is attached to the lead body 10. Lead body 10 contains the electrical conductors which couple the pressure transducer head 50 to the associated electronic circuitry. The conductors are coils to reduce bending stress and, thus, decrease flex breakage. Lead body 10 terminates in the four conductors 12, 14, 16 and 18 each of which is terminated by an electrical connector body (i.e., 20, 22, 24 and 26 respectively) with an associated connection pin (i.e., 28, 30, 32 and 34, respectively). In keeping with the practices in the fabrication of implantable pacing leads for chronic application, lead body 10 and the four conductors 12, 14, 16 and 18, are coated with a material substantially inert to boby fluids such as silicon rubber or urethane. Connector bodies 20, 22, 24 and 26 also contain O-rings 36 for sealing the electrical connections against ingress of body fluids. Connector body 10 is sealed to pressure transducer head 50 by the injection molding of silicon rubber.

FIG. 2 shows the electrical characteristics of the pressure transducer. Notice that electrically the circuit is a resistive bridge represented by fixed resistors 40, 42, 44 and 46. Each point of the bridge is connected to a different one of the interface leads 48a, 48b, 48c and 48d. As the measured pressure changes, the relative resistance of the resistive bridge legs change which is sensed via interface leads 48a, 48b, 48c and 48d.

Figure 3:
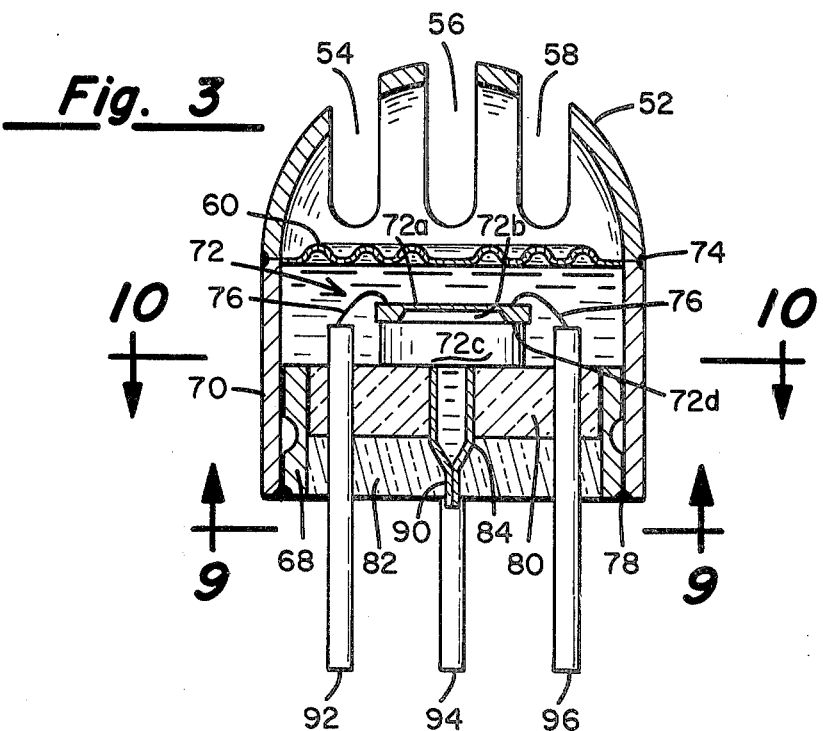
FIG. 3 is a side sectional view of the preferred embodiment of the pressure transducer head 50.

FIG. 3 is a side sectional view of the pressure transducer head 50 in the preferred embodiment having a sealed inner chamber. The basic pressure transducer 72 is mounted internal to the pressure transducer head 50. The basic pressure transducer 72 is available commercially. U.S. Pat. No. 4,023,562 issued to Hynecek, et al, teaches the construction and operation of a suitable basic pressure transducer 72, although electrical coupling is made via wire bonding in the present invention and not via the chip holder used in the reference. The basic pressure transducer is comprised of upper silicon diaphragm 72a which flexes with pressure changes, sealed inner chamber 72b, silicon substrate 72c, and hermetic bond 72d. Basic pressure transducer 72 is adhesively bonded to a glass substrate 80. A glass having nearly the same temperature coefficient of expansion as silicon is chosen, such as Corning 7070. Lead-in conductors 92, 94, 96 and 98 are electrically coupled to basic pressure transducer 72 via common wire bonds 76. Notice that lead-in conductor 98 is directly opposite lead-in conductor 94 and is not shown in the sectional view. Also the wire bonds are clearly visible for only lead-in conductors 92 and 96. Each of the lead-in conductors (i.e., 92, 94, 96 and 98) is electrically coupled to a different one of four separate conductors located within lead body 10 and thence to one of connection pins 28, 30, 32 and 34 (see also FIG. 1).

Referring again to FIG. 3, one can see that glass substrate 80 is adhesively attached to pressure transducer base 82 which may be made of titanium, ceramic, or other suitable material. Glass is presently used because using an insulator obviates the need to insulate the feed-through holes for lead-in conductors 92, 94, 96 and 98. The glass base is encased in header 68 which is a cylinder of titanium.

Header 68 is inserted into a titanium outer cylinder 70. The outer cylinder is sealed about its inner circumference to header 68 by weld 78. A titanium diaphragm 60 seals the opposite end to outer cylinder 70. Weld 74 seals the entire outer circumference and also attaches grill 52, provided the grill is metal and not polymer.

Tube 84 is used to vacuum fill the entire chamber thus created with oil. In the preferred embodiment glass substrate 80 has sawed-in grooves to permit filling (see also FIG. 10). Tube 84 is pinched and welded shut after vacuum filling creating seal 90. It is important that this inner chamber be vacuum filled to properly transmit pressure changes.

Body fluid into which pressure transducer head 50 is immersed, freely enters grill 52 via slots 54, 56 and 58 impinging upon diaphragm 60. The pressure of that body fluid is transmitted by the oil with the outer chamber to basic pressure transducer 72. That pressure is measured against the calibrated pressure of the sealed inner chamber 72b by flexing of silicon diaphragm 72a. This flexing results in electrical changes measured as resistive changes in the resistive bridge circuit of FIG. 2.

Figure 4:
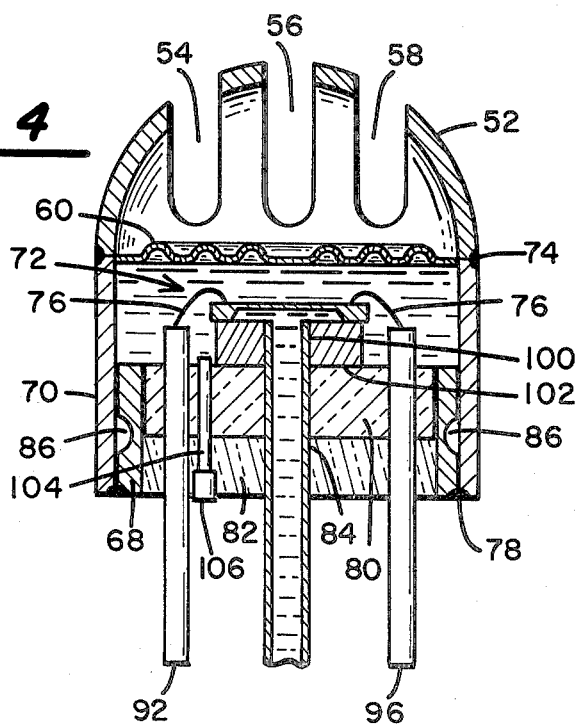
FIG. 4 is a side sectional view of the alternate embodiment of the pressure transducer head 50 which measures differential pressure.

FIG. 4 provides an equivalent side sectional view of the alternative embodiment used to measure differential pressure. The structure is identical except that basic pressure transducer 72 is vented. To accomplish this an aperture 100 is created in the silicon substrate 72c which is coupled to tube 84, coupling inner chamber 72b to tube 84. Tube 84 is not sealed but is instead coupled to a corresponding tube within lead body 10 as explained below. Since tube 84 must be sealed from the oil filled interior of outer cylinder 70, no sawed-in grooves exist in glass substrate 80 and the device must be vacuum filled through tube 104 drilled through base 82 and glass substrate 80. Plug 106 is used to seal tube 104. In fabricating the alternative embodiment, case must be exercised in creating seal 102 between the silicon substrate 72c of basic pressure transducer 72 and glass substrate 80.

Figure 5:
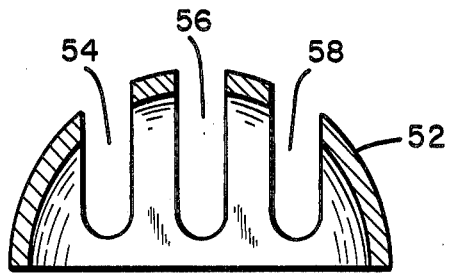
FIG. 5 is a top view of the protecting grill.
Figure 6:
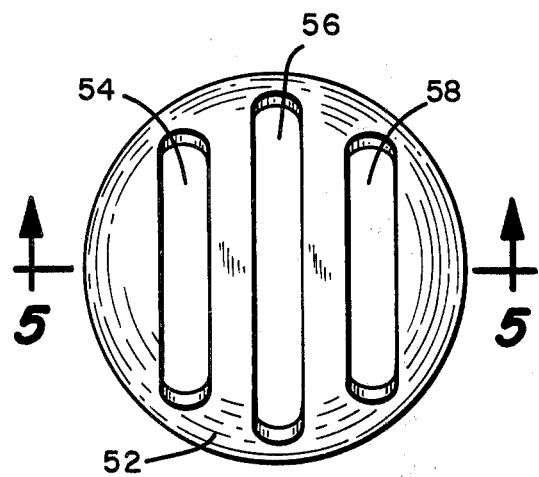
FIG. 6 is a side sectional view of the protecting grill.

FIG. 5 is a top view of grill 52 with slots 54, 56 and 58 visible. FIG. 6 provides a side sectional view of grill 52. The present material used is titanium although stainless steel or a polymer like urethane would also seem feasible. The principal purpose of grill 52 is protection of diaphragm 60, and to aid in sliding down an artery or vein. This protection is most critical during implantation, although chronic protection is also required because of anticipated movement. Grill 52 must have openings to permit impingement of body fluid upon diaphragm 60. It is important that these openings permit smooth flow of body fluids to ensure cleansing of diaphragm 60 of any solid material such as small blood clots. The present design uses slots 54, 56 and 58, although other shapes are also acceptable.

Figure 7:
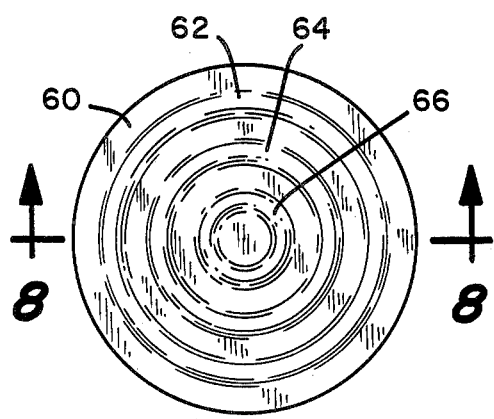
FIG. 7 is a top view of the titanium diaphragm.
Figure 8:
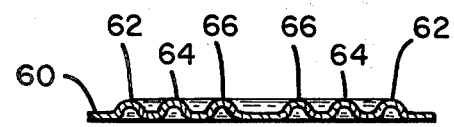
FIG. 8 is a side sectional view of the titanium diaphragm.

FIG. 7 is a top view of diaphragm 60. It is a titanium disc having a diameter of about one fourth inch having a thickness of 1–2 mils. It is important that a material be used which is sufficiently thin and flexible to properly transmit the pressure changes of the bodily fluid while having sufficient tensile strength to provide a chronic seal. To increase the compliance (flexibility) of diaphragm 60, ridges 62, 64 and 66 are stamped into the disc as shown. The side sectional view provided in FIG. 8 shows ridges 62, 64 and 66 which are about five one-thousandths of an inch in height.

Figure 9:
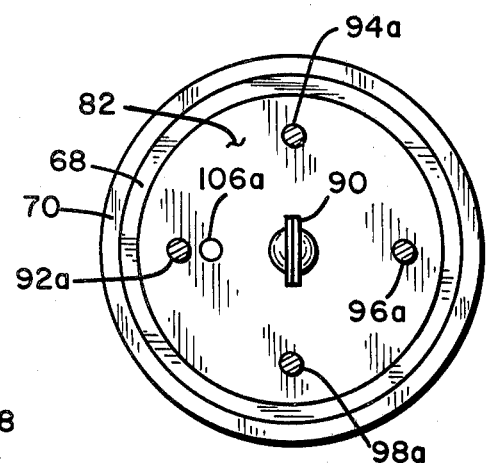
FIG. 9 is a bottom view of glass substrate 82.

FIG. 9 is a bottom sectional view of pressure transducer head 50 showing pressure transducer base 82. As explained above, use of glass or other insulator for pressure transducer base 82 obviates the need to insulate feedthrough holes 92a, 94a, 96a and 98a. For the preferred embodiment (see also FIG. 3), tube 84 is pinched and welded creating seal 90. For the alternative embodiment (see also FIG. 4), tube 84 is extended and coupled to a corresponding tube in lead body 10 so no seal 90 exists. Furthermore, aperture 106a is added to permit the chamber to be oil-filled.

Figure 10:
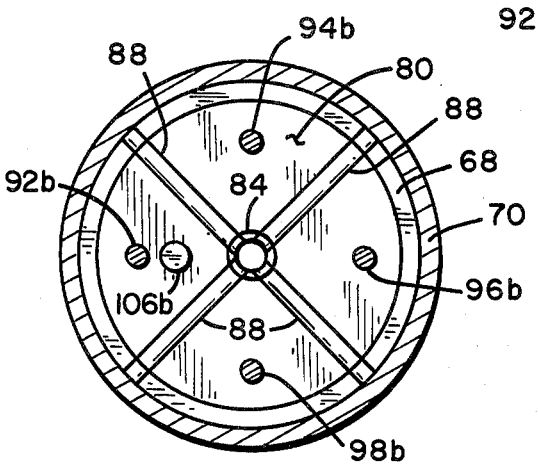
FIG. 10 is a top view of case bottom 80.

FIG. 10 is a top sectional view of pressure transducer head 50 showing glass substrate 80. In the preferred embodiment, sawed-in grooves 88 are provided for the oil-filling of the chamber. Oil which is supplied by tube 84 travels under silicon 72c, which is adhesively bonded to glass substrate 80, via sawed-in grooves 88. In the alternate embodiment, tube 84 and the chamber must be isolated so no sawed-in grooves 88 are formed. The chamber is oil-filled via aperture 106b. Apertures 92b, 94b, 96b and 98b are feedthrough holes for lead-in conductors 92, 94, 96 and 98, which are sealed after insertion.

FIG. 11 shows a differential pressure measuring lead of the alternate embodiment having an appearance similar to the preferred embodiment (see also FIG. 1). The alternate embodiment requires tube 118 (shown in dashed lines) to be present within lead body 10. Tube 118 is coupled to tube 84 (see also FIG. 4) to vent inner chamber 72b of basic pressure transducer 72. Tube 118 is vented via silastic membrane 49. Inner chamber 72b, tube 84, and tube 118 are vacuum filled with oil. This oil transmits pressure variations from silastic membrane 49 to inner chamber 72b l and silicon diaphragm 72a via tubes 118 and 84, thus permitting differential pressure measurements.

Figure 12:
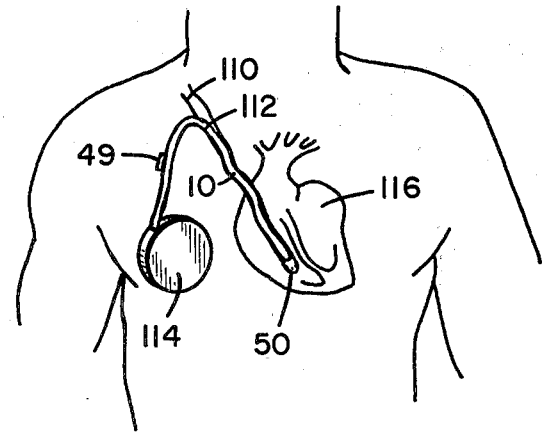
FIG. 12 is a schematic view of a typical application of the present invention.

FIG. 12 shows a typical application for the present invention. An incision is made permitting access to vein 110. Incision 112 is made in vein 110. Pressure transducer head 50 is inserted into heart 116 via vein 110. The remainder of lead body 10 extends from incision 112 to implantable electronic circuit 114 and is electrically coupled thereto. In the present embodiment, the pressure of blood within the right ventricle of heart 116 relative to the pressure within inner chamber 72b may thus be sensed by implantable electronic circuit 114. Tines 50a or other position maintaining structures may be arranged appurtenant to pressure transducer head 50 in accordance with techniques for transvenous implantation of pacing leads. Implantation of a lead employing the alternate embodiment is similar except that care must be taken to position silastic membrane 49 to properly vent inner chamber 72b in the desired body cavity.

What is claimed is:

1. An implantable pressure transducer comprising:
   a sealed container having a flexible wall fully filled with a first liquid;
   lead-in conductors exposed to the exterior of said container;
   a basic pressure transducer having a sensing surface and a vent and coupled to said lead-in conductors, wherein pressure impinging on said sensing surface relative to pressure impinging on said vent may be electrically detected from said lead-in conductors, said transducer fixedly mounted to said container with said first liquid impinging on said sensing surface and with said vent exposed to the exterior of said container;
   conductor means for coupling said transducer to associated electronic circuitry, coupled to said lead-in conductors;
   connectors electrically coupled to said conductor means;
   a vent tube having a first end and a second end, fully filled with a second liquid, said first end sealably coupled to said vent, said second liquid impinging on said vent;
   a membrane sealably coupled to the second end of said vent tube whereby the pressure differential between pressure external to said container and to said membrane may be electrically detected from said connectors; and
   a lead body of a material substantially inert to body fluid encasing said conductor means and said vent tube, said lead body having an aperture wherein said membrane is exposed to the exterior of said lead body, said lead body fixedly mounted to said container and to said connectors.

2. An implantable pressure transducer according to claim 1 wherein said first liquid and said second liquid are the same substance.

3. An implantable pressure transducer according to claim 1 or claim 2 wherein said basic pressure transducer is mounted within said container.

4. An implantable pressure transducer according to claim 3 further comprised of a substrate fashioned of a substance having a coefficient of thermal expansion similar to that of said basic pressure transducer wherein said basic pressure transducer is fixedly mounted to said substrate.

5. An implantable pressure transducer according to claim 4 wherein said substrate is mounted entirely within said container and fixedly attached to said container.

6. An implantable pressure transducer according to claim 5 wherein said substrate is adhesively attached to said container.

7. An implantable pressure transducer according to claim 6 wherein said first liquid and said second liquid are both oil.

* * * * *

UNITED STATES PATENT AND TRADEMARK OFFICE
CERTIFICATE OF CORRECTION

PATENT NO. : 4,407,296
DATED : October 4, 1983
INVENTOR(S) : Kenneth M. Anderson It is certified that error appears in the above-identified patent and that said Letters Patent are hereby corrected as shown below:

[54] "INTEGRAL HERMETIC IMPANTABLE PRESSURE TRANSDUCER" should be --INTEGRAL HERMETIC IMPLANTABLE PRESSURE TRANSDUCER--;

Column 1,
 line 1, "IMPANTABLE" should be --IMPLANTABLE--;

Column 4,
 line 60, "72b 1 and silicon diaphragm 72a" should be --72b and silicon diaphragm 72a-- (no italics);

Signed and Sealed this

Twenty-second Day of May 1984

[SEAL]

Attest:

GERALD J. MOSSINGHOFF

*Attesting Officer*     *Commissioner of Patents and Trademarks*